United States Patent
Nakanishi et al.

(10) Patent No.: US 6,917,665 B2
(45) Date of Patent: Jul. 12, 2005

(54) X-RAY COMPUTED TOMOGRAPHY APPARATUS

(75) Inventors: Satoru Nakanishi, Tochigi-ken (JP);
Keiji Matsuda, Tochigi-ken (JP);
Yasutaka Shindo, Tochigi-ken (JP);
Miwa Okumura, Tochigi-ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 10/283,103

(22) Filed: Oct. 30, 2002

(65) Prior Publication Data

US 2003/0091157 A1 May 15, 2003

(30) Foreign Application Priority Data

Oct. 31, 2001 (JP) ........................................ 2001-335848

(51) Int. Cl.[7] .............................................. G01N 23/00

(52) U.S. Cl. .............................................. 378/19; 378/4

(58) Field of Search ........................................ 378/19, 4

(56) References Cited

U.S. PATENT DOCUMENTS 6,056,437 A * 5/2000 Toth ............................ 378/205
6,327,331 B1 * 12/2001 Toth et al. ..................... 378/20
6,370,218 B1 * 4/2002 Toth et al. ..................... 378/19

FOREIGN PATENT DOCUMENTS

JP 9-201353 8/1997
JP 2002-172091 6/2002

* cited by examiner

*Primary Examiner*—Craig E. Church
(74) *Attorney, Agent, or Firm*—Oblon, Spivak, McClelland, Maier & Neustadt, P.C.

(57) ABSTRACT

An X-ray computed tomography apparatus for providing information of alignment, comprises an X-ray generator, an X-ray detector, and a controller. The X-ray generator generates an X-ray. The X-ray detector comprises a plurality of detecting segments in a slice direction and detects the X-ray generated by the X-ray generator. The controller provides the information of alignment between the X-ray generator and the X-ray detector in the slice direction on the basis of a detection information obtained from at least two of the detecting segments, wherein each of the at least two of the detecting segments is at least partially covered by a penumbra of the X-ray.

11 Claims, 9 Drawing Sheets

→ SLICE DIRECTION(OBJECT'S BODY AXIS DIRECTION)

→ SLICE DIRECTION(OBJECT'S BODY AXIS DIRECTION)

→ SLICE DIRECTION

X-RAY COMPUTED TOMOGRAPHY APPARATUS

CROSS-REFERENCE TO RELATED APPLICATION

This application is based upon and claims the benefit of priority from prior Japanese Patent Application No. P2001-335848, filed on Oct. 31, 2001, the entire content of which is incorporated herein by reference.

FIELD OF THE INVENTION

The present invention relates to an X-ray computed tomography apparatus which has an X-ray tube and a multi-slice X-ray detector provided to face to each other. The present invention further relates to a method of obtaining information of a physical relationship between the X-ray tube and the multi-slice X-ray detector.

BACKGROUND OF THE INVENTION

An X-ray computed tomography apparatus (hereinafter referred to as CT apparatus) is known to provide images of information from an examination object, such as a patient, (hereinafter referred to as object) based on the intensity of an X-ray transmitted through the object. The images provided by the CT apparatus play an important part in a lot of medical practices including a diagnosis of a disease, a treatment, and a medical operation planning. Imaging by the CT apparatus is now realized by, for example, a multi-slice scanning and a helical scanning as the latest technique. The multi-slice scanning is a technique of obtaining a plurality of projection data of the object in a single rotation scanning. The helical scanning is a technique of obtaining projection data of a wide range of the object by scanning the object in a helical manner.

A multi-slice scanning CT apparatus usually requires alignment of its multi-slice X-ray detector, as needed, in the following exemplary manner, so as to keep a preferable scanning condition.

FIG. 1 is an example showing a physical relationship between an X-ray tube and an X-ray detector in a conventional multi-slice CT apparatus according to a prior art. In FIG. 1, a slit 200 may be adjusted, for example, so that an X-ray irradiated from an X-ray tube 204 can be exposed to an X-ray detector 202 in order to obtain four slices each of which has a 2 mm width (i.e. 2 mm×4 slices) in a direction of the object body axis in each scanning. The X-ray detector 202 may obtain an output value α in the above condition. Further, the slit 200 may also be adjusted, for example, so as to obtain four slices each of which has an 8 mm width (i.e. 8 mm×4 slices) in each scanning, and under this condition an X-ray irradiated from the X-ray tube 204 can be exposed to the X-ray detector 202 which is prepared to detect four slices each of which has a 2 mm width (i.e. 2 mm×4 slices), in each scanning. The X-ray detector 202 may obtain an output value β in the above condition. It is a conventional technique of alignment between the X-ray tube 204 and the X-ray detector 202 that a ratio α/β is approximated to 1 in every detecting segment of the X-ray detector 202. In this alignment, it may be possible to adjust and/or confirm whether the X-ray irradiated from the X-ray tube 204 is exposed to a predetermined operative area of the X-ray detector 202 or not (whether the predetermined operative area of the X-ray detector 202 in the direction of the object's body axis is covered by an umbra of the X-ray irradiated from the X-ray tube 204).

According to the above-mentioned conventional alignment, however, it is not possible to adjust to match a central axis of the X-ray irradiated from the X-ray tube 204 and the center of the X-ray detector 202 in the direction of the object's body axis. Therefore, an aperture width of the slit 200 may be required to be wider than a necessary width of the aperture in each data acquisition mode (for example, 2.0 mm×4 slices in a single rotation scanning). This may cause the object to be exposed to radiation excessively.

BRIEF SUMMARY OF THE INVENTION

According to a first aspect of the present invention, there is provided an X-ray computed tomography apparatus for providing information of alignment, which comprises an X-ray generator for generating an X-ray, an X-ray detector, comprising a plurality of detecting segments in a slice direction, for detecting the X-ray generated by the X-ray generator, and a controller for providing the information of alignment between the X-ray generator and the X-ray detector in the slice direction on the basis of a detection information obtained from at least two of the detecting segments, wherein each of the at least two of the detecting segments is at least partially covered by a penumbra of the X-ray.

According to a second aspect of the present invention, there is provided a method of obtaining information of alignment between an X-ray generator and an X-ray detector of an X-ray computed tomography apparatus for producing a multi-slice scanned image, wherein the X-ray generator generates an X-ray and the X-ray detector comprises a plurality of detecting segments in a slice direction and detects the X-ray generated by the X-ray generator, which comprises steps of obtaining a detection information from at least two of the detecting segments, wherein each of the at least two of the detecting segments is at least partially covered by a penumbra of the X-ray, calculating an information of alignment between the X-ray generator and the X-ray detector in the slice direction on the basis of the detection information obtained in the obtaining step, and providing the information of alignment calculated in the calculating step.

According to a third aspect of the present invention, there is provided An X-ray computed tomography apparatus for providing information of alignment, which comprises an X-ray generator for generating an X-ray, a slit for collimating the X-ray, the slit having a variable aperture width, an X-ray detector for detecting the X-ray collimated by the slit, and a controller for providing the information of alignment between the X-ray generator and the X-ray detector in a slice direction on the basis of a first detection information obtained from the X-ray detector when the slit collimates the X-ray generated by the X-ray generator with a first aperture width and a second detection information obtained from the X-ray detector when the slit collimates the X-ray generated by the X-ray generator with a second aperture width.

According to a fourth aspect of the present invention, there is provided an X-ray computed tomography apparatus for providing information of alignment, which comprises an X-ray generator for generating an X-ray, a slit for collimating the X-ray generated by the X-ray generator with a variable aperture width, an X-ray detector for detecting the X-ray collimated by the slit, and a controller for providing the information of alignment between the X-ray generator and the X-ray detector in a slice direction on the basis of a detection information obtained from the X-ray detector when the slit collimates the X-ray generated by the X-ray generator with a first aperture width different from a second aperture width used for producing a multi-slice scanned image of an object in the slice direction.

BRIEF DESCRIPTION OF THE DRAWINGS

A more complete appreciation of embodiments of the present invention and many of its attendant advantages will be readily obtained by reference to the following detailed description considered in connection with the accompanying drawings, in which.

DETAILED DESCRIPTION OF THE PREFERRED EMBODIMENTS

Embodiments of the present invention will be described with reference to the accompanying drawings.
(First Embodiment)

Generally, various types of configurations may be known for CT apparatuses. The following are examples of such known CT apparatuses: a rotate/rotate type where an X-ray tube and an X-ray detector rotate around an object as a unit; a stationary/rotate type where only an X-ray tube rotates around the object, with many X-ray detecting elements arrayed in a form of a ring; and a type where an X-ray tube is electronically moved on a target by deflecting an electronic beam. An embodiment of the present invention can be applied to any type of these configurations. As long as a CT apparatus has an X-ray detector which can be used for a multi-slice scanning and an X-ray tube, an embodiment of the present invention may be applied to such a CT apparatus. The rotate/rotate type, which is currently popular, is taken as an example of such a CT apparatus for use with an embodiment of the present invention.

Figure 1:
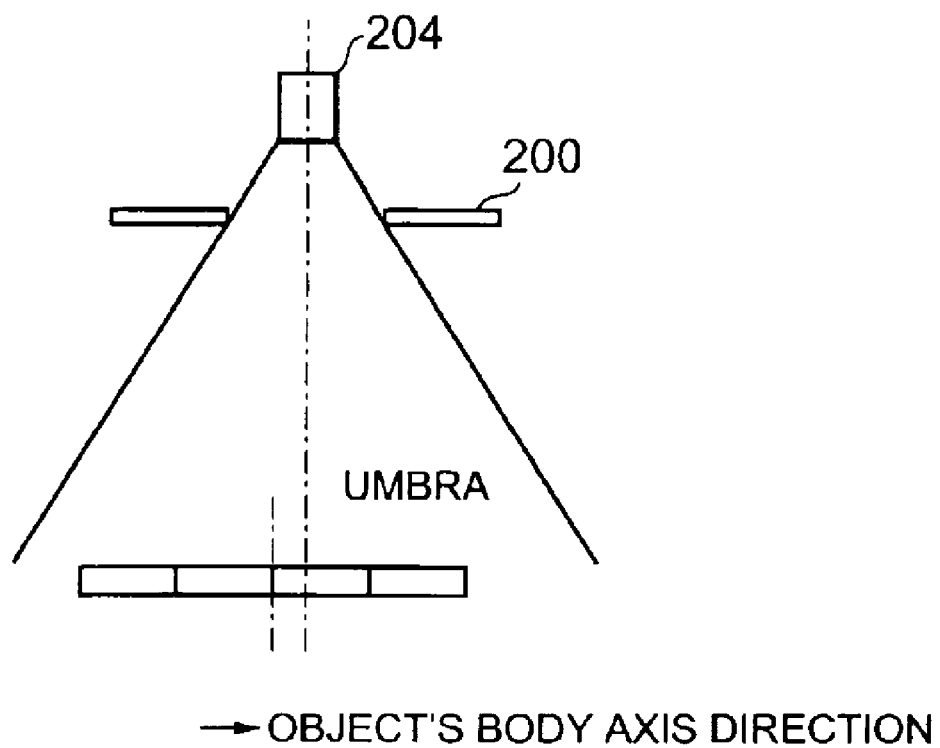
FIG. 1 is an example showing a physical relationship between an X-ray tube and an X-ray detector in a conventional multi-slice CT apparatus according to a prior art.
Figure 2:
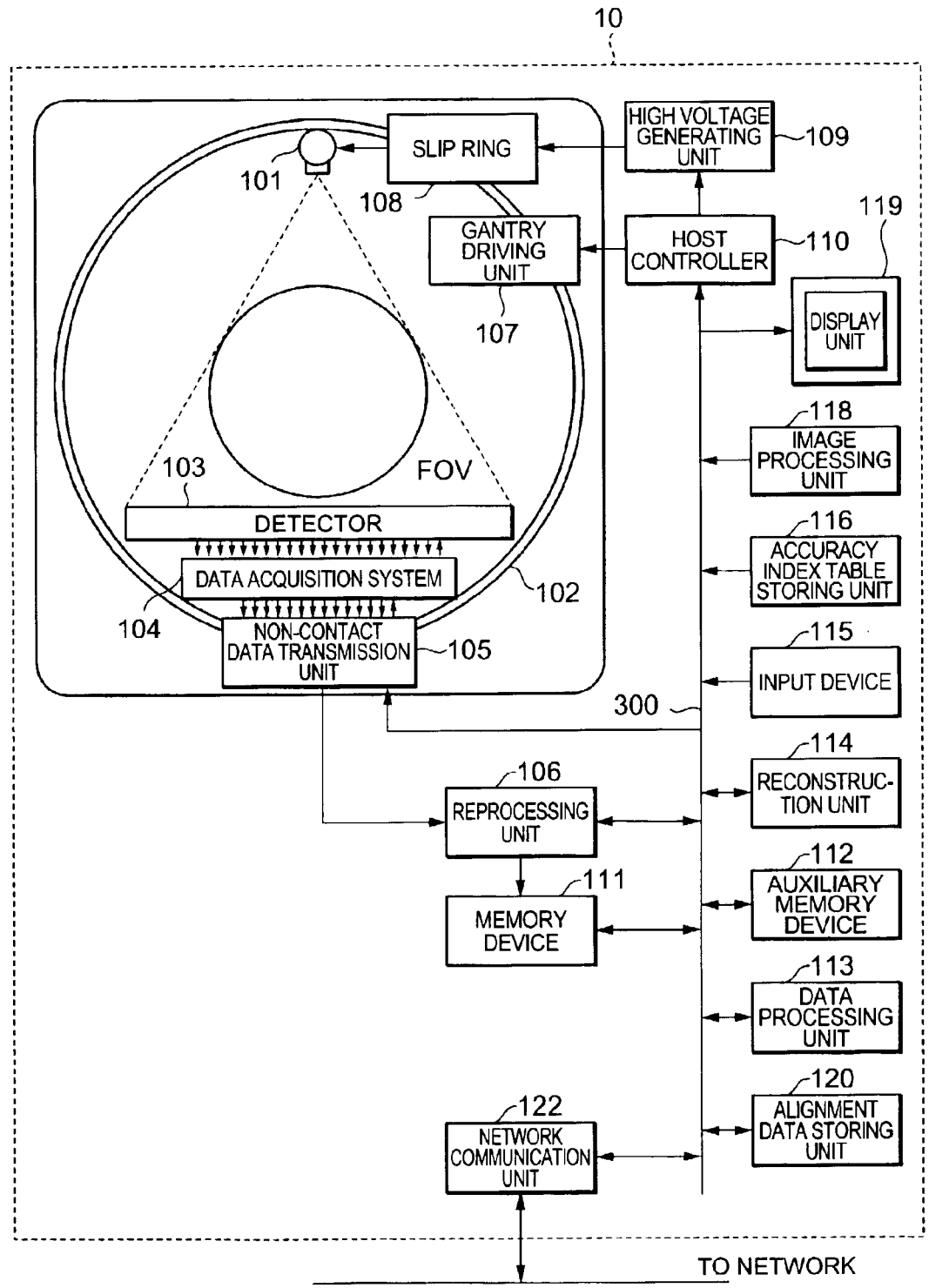
FIG. 2 is a block diagram showing a CT apparatus according to a first embodiment of the present invention.
Figure 3:
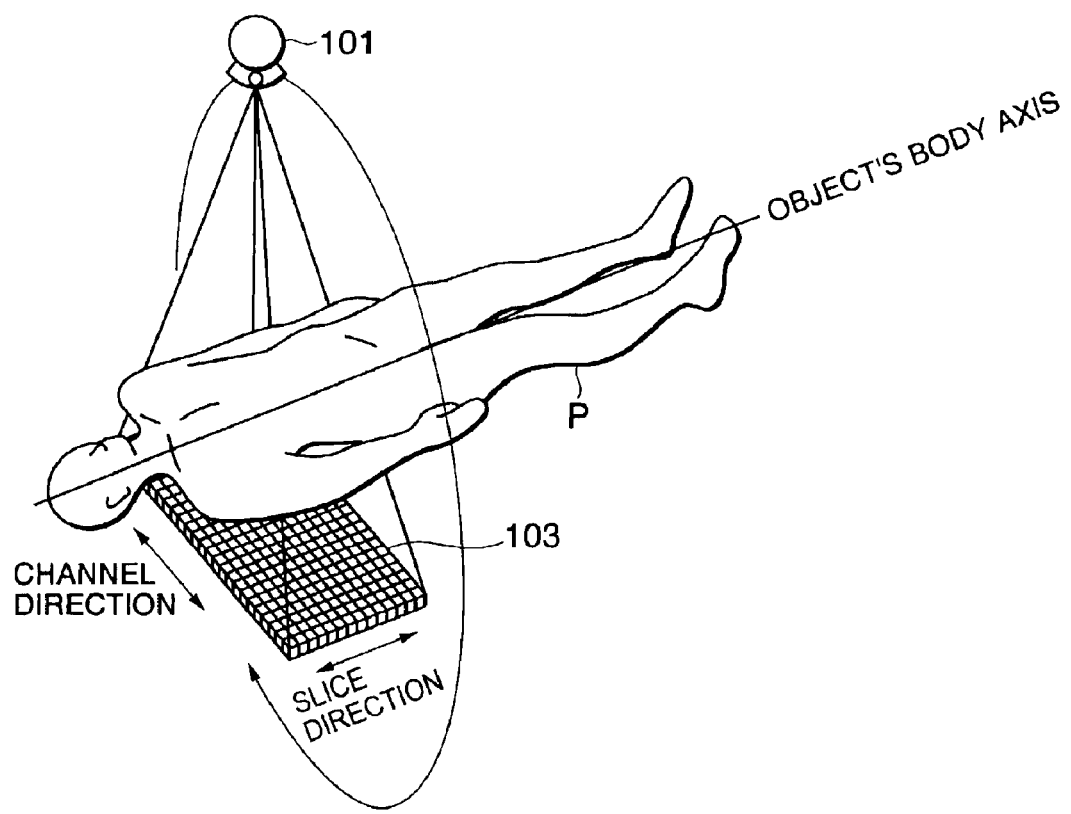
FIG. 3 is an example showing radiography of tomographs by the CT apparatus according to the first embodiment of the present invention.

FIG. 2 is a block diagram showing a CT apparatus according to a first embodiment of the present invention. Further, FIG. 3 is an example showing radiographing tomographs by the CT apparatus shown in FIG. 2 according to the first embodiment of the present invention.

As shown in FIG. 2, a CT apparatus 10 comprises an X-ray tube 101, a rotation ring 102, a two-dimensional X-ray detecting system (hereinafter referred to as detector) 103, a data acquisition system 104, a non-contact data transmission unit 105, a preprocessing unit 106, a gantry driving unit 107, a slip ring 108, a high voltage generating unit 109, a host controller 110, a memory device 111, an auxiliary memory device 112, a data processing unit 113, a reconstruction unit 114, an input device 115, an accuracy index table storing unit 116, an image processing unit 118, a display unit 119, an alignment data storing unit 120, a network communication unit 122, and a data/control bus 300.

The X-ray tube 101 is a vacuum bulb which generates an X-ray and is mounted on the rotation ring 102. The X-ray tube 101 is supplied with power necessary for X-ray radiation from the high voltage generating unit 109 through the slip ring 108. The X-ray tube 101 accelerates electrons with the supplied high voltage and makes the electrons collide with a target. Accordingly, the X-ray tube irradiates the X-ray in a conical form towards the object P placed in its field of view (FOV).

It may be preferable to align the X-ray tube 101 with the detector 103 so as to match the central axis of the X-ray beam irradiated from the X-ray tube 101 and the center of the detector 103 in order to achieve more accurate radiography. This matching may be achieved by an alignment processing described later.

In addition, the X-ray beam irradiated from the X-ray tube 101 can be collimated by a slit 121 shown in FIGS. 4 and 5 both of which will be explained later.

On the rotation ring 102, there are mounted the X-ray tube 101, the detector 103, and the data acquisition system 104. The rotation ring 102 is driven by the gantry driving unit 107 and rotates with the X-ray tube 101 and the detector 103 around an object P at a speed of less than one second per rotation.

The detector 103 is a detecting system for detecting an X-ray transmitted through the object P, and is mounted on the rotation ring 102, facing to the X-ray tube 101. The detector 103 comprises a plurality of detecting elements, for example, constituted by a combination of scintillators and photodiodes. The detecting elements are typically arrayed in two-dimensions, along the object's body axis direction and along a channel direction orthogonal with the object's body axis. For example, one thousand (one thousand channels) detecting elements are arrayed, in every row of the two dimensional detector 103, along the channel direction of an example detector. One row of the detector 103 (for example, comprising the one thousand detecting elements) is hereinafter referred to as detecting element row.

Further, the detector 103 may be aligned with the X-ray tube 101 by the alignment processing described later in order to achieve more accurate radiography.

The data acquisition system 104 comprises a plurality of DAS (data acquisition system) chips. The data acquisition system 104 takes in a flood of data detected by the detector 103. The data detected by the detector 103 may be data regarding, for example, M×N channels, of the detector 103. Here M is the number of detecting elements in the channel direction and N is the number of detecting elements in the slice direction (in the object's body axis direction). The data acquisition system 104 processes the taken-in data, such as amplification and analog-to-digital processing. After the processing, the processed data are sent to the units that follow through the non-contact data transmission unit 105 which applies optical communications.

The non-contact data transmission unit 105 optically transmits the data received from the data acquisition system 104 to the units that follow. The data acquisition system 104 and the non-contact data transmission unit 105 are designed to make a very high speed processing so as to transmit the flood of data, even generated at a high speed in the detector 103, without delay. That is, the X-ray transmitted through the object is converted to analog electric signals in the detector 103 and the converted analog electric signals are converted to digital electric two-dimensional projection data in the data acquisition system 104. After these conversions, the two-dimensional projection data are sent, through the non-contact data transmission unit 105, to the preprocessing unit 106 which performs several corrections.

The preprocessing unit 106 receives the two-dimensional projection data from the non-contact data transmission unit 105 and performs preprocessing, such as a sensitivity correction and an X-ray intensity correction. The preprocessed two-dimensional projection data are sent to the data processing unit 113 directly or, alternatively, indirectly through or without through the storage in the memory device 111.

The gantry driving unit 107 drives the rotation ring 102 and so on provided in a gantry of the CT apparatus 10, so that the X-ray tube 101 and the detector 103 are rotated together along an axis in parallel with the axis direction of the object P who is placed inside the aperture of the rotation ring 102. In other configuration of the CT apparatus, the gantry driving unit 107 may drive the rotation ring only with an X-ray tube.

The high voltage generating unit 109 supplies a power (high voltage) necessary for X-ray radiation with the X-ray tube 101 through the slip ring 108. The high voltage generating unit 109 comprises high voltage transformers, filament heating transducers, rectifiers, high voltage switches, and so on.

The host controller 110 controls overall several kinds of processing, such as radiographic processing, data processing, and image processing. For example, in radiographic processing, the host controller 110 stores scanning conditions, such as a slice thickness which was input in advance, in an internal memory. Further, for example, the host controller 110 controls the high voltage generating unit 109, a bed driving unit (not shown), the gantry driving unit 107, a distance to move a bed along the object's body axis direction, its moving speed, a rotation speed of the X-ray tube 101 and the detector 103, its rotation pitch, a timing of the X-ray radiation, and so on, on the basis of the scanning condition automatically selected according to a patient ID or the like (or the scanning condition directly set by the input device in a manual mode). Accordingly, the X-ray beam in the conical form is exposed to a desired region of the object P from various directions and radiographic processing is performed for obtaining X-ray CT images.

Furthermore, the host controller 110 controls switches included in the detector 103 on the basis of the scanning conditions. To be more specific, the host controller 110 controls the switches to switch connections between each detecting element and each data acquisition element, both of which are included in the detector 103, and to bundle data detected by the detecting elements in a predetermined unit. The bundled data are sent to the data acquisition system 104 as data obtained, with X-ray transmitted through the object, in a predetermined plurality of slices according to the scanning condition. The data acquisition system 104 processes the data, such as described above.

Still further, the host controller 110 calculates a ratio of predetermined signals in the alignment processing described later and compares the ratio to an accuracy index table prepared in advance which is stored in the accuracy index table storing unit 116. Accordingly, the host controller 110 obtains a distance to move either the X-ray tube 101 or the detector 103 along the slice direction.

The auxiliary memory device 112 has a large capacity of memory area which can store reconstructed image data produced in the reconstruction unit 114.

The data processing unit 113 has computer circuitry, including a CPU (central processing unit), and holds projection data of a predetermined number of slices acquired in the detector 103. The data processing unit 113 adds every projection data, of a slice, obtained from multiple directions by rotating the X-ray tube 101 and the detector 103, for each slice. Further, the data processing unit 113 performs processing, such as interpolation and correction, for the multi direction data obtained in the addition processing.

The reconstruction unit 114 reconstructs the projection data obtained through the data processing in the data processing unit 113, and produces reconstructed image data of a predetermined number of slices. To be more specific, the reconstruction unit 114 may perform a two-dimensional image reconstruction processing or a reconstruction processing by a three-dimensional image reconstruction algorithm, for example, represented by the Feldkamp theorem. The reconstruction unit 114 reconstructs two-dimensional distribution data of X-ray absorption coefficients for each of a plurality of cross sections coming across the object along the object's body axis direction. Alternatively, the reconstruction unit 114 reconstructs three-dimensional distribution data of X-ray absorption coefficients in a target area (volume) which ranges broadly in the object's body axis direction. The three-dimensional distribution data are the gathering of three-dimensional volume data represented by voxels, and are commonly called 'voxel volume data'. In addition, the reconstruction unit 114 reconstructs a tomograph, based on projection data obtained from multiple directions which are necessary to reconstruct the tomograph, in a shorter time than a time required to acquire such projection data. This reconstruction processing may be called real time reconstruction processing.

The input device 115 may comprise a keyboard, several switches, and a mouse. The input device 115 allows an operator to input various scanning conditions, such as slice thickness and the number of slices.

The accuracy index table storing unit 116 stores an alignment accuracy index table which is used in the alignment processing described later. The alignment accuracy index table is prepared by, for example, a predetermined simulation in advance, and is used for obtaining a distance to move (or adjust) the X-ray tube 101 or the detector 103.

The image processing unit 118 performs image processing, such as a window conversion (a gray scale conversion) and RGB processing, for the reconstructed image data produced in the reconstruction unit 114. The image processed data are output to the display unit 119. Further, the image processing unit 118 produces, in accordance with designations by the operator, pseudo-three dimensional images, such as tomographs according to a given cross section of the object, projection images from given directions, and three-dimensional surface images. The produced images are output to the display unit 119. The output images are displayed as X-ray CT images in the display unit 119.

The alignment data storing unit 120 stores data resulted from the alignment processing described later.

The network communication unit 122 communicates with external apparatuses which equip communication features through a network, such as a hospital's internal LAN (local area network) and the Internet. Particularly, the network communication unit 122 may be useful when it is used to inform, through the Internet or the like, a communication equipment of a service provider who maintains the CT apparatus 10, of necessity of the alignment processing, as explained later in a second embodiment of the present invention.

Those skilled in the art will understand the following general processes implemented in the CT apparatus 10: the reconstruction processing; the data processing, such as a cross section conversion; the display operation; the calculation regarding the alignment processing described later; and so on. However, it may be possible to implement the above processing in an external image processing unit, such as a workstation. In this case, data transmitted from the CT apparatus 10 to such an external image processing unit can be either of not-reconstructed data, already-reconstructed data, or data ready to be displayed. Any form of data described above can be applied to the embodiment of the present invention.

[Alignment Processing]

Next, the alignment processing (or method) in the CT apparatus 10 will be described below. In the alignment processing, the relative location between the X-ray tube 101 and the detector 103 are adjusted so as to match the central axis of the X-ray beam in the conical form irradiated from the X-ray tube 101 and the center of the detector 103.

In the first embodiment of the present invention, the multi-slice scanning may be performed, for example, with a four-slice scanning (i.e., four slices of tomographs are obtained in each rotation of the scanning). Each slice may be obtained with the detecting elements in a plurality of the detecting element rows of the detector 103, such as 8 detecting element rows, 16 detecting element rows, 34 detecting element rows, 40 detecting element rows, and 250 detecting element rows. For example, when one detecting element has a width to detect a 0.5 mm width, 4 detecting element rows of the detecting elements are required to detect a 2 mm width slice. Such detecting element rows for a slice may be called a detecting segment. As shown in FIG. 3, in the multi-scanning, the X-ray tube 101 and the detector 103 rotate around the object P and a plurality of tomographs are acquired.

Figure 4:
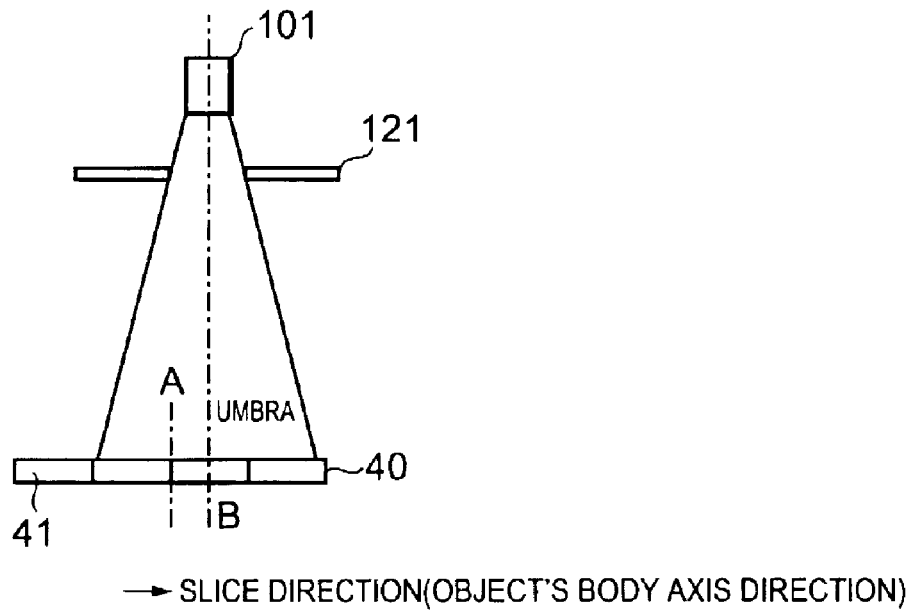
FIG. 4 is an example showing a physical relationship between an X-ray tube and a detector for explaining an umbra according to the first embodiment of the present invention.

FIG. 4 is an example showing a physical relationship between the X-ray tube 101 and the detector 103 according to the first embodiment of the present invention. If the central axis B of the X-ray beam irradiated from the X-ray tube 101 and the center A of four detecting segments 40 of the detector 103 are out of alignment in the slice direction (the object's body axis direction), the X-ray may not be exposed to all of the four detecting segments 40. As shown in FIG. 4, the X-ray is not exposed to one segment 41 of the four detecting segments 40. If this happens, preferable tomographs can not be obtained. To avoid unnecessary excessive X-ray exposure to the object P, it is desired that the aperture of a slit 121 to collimate the X-ray may be as narrow as possible, only as required in accordance with its scanning width. Therefore, it is desired to match the central axis of the X-ray beam irradiated from the X-ray tube and the center of the then used detecting segments in the slice direction.

In addition, as shown in FIG. 4, when the central axis B is construed as a symmetry axis, an umbra is deemed to be an X-ray radiation field between a line extended from one end of the X-ray tube 101 through an end of the aperture of the slit 121 on the same side to the central axis B and a line extended from the other end of the X-ray tube 101 through the other end of the aperture of the slit 121.

Figure 5:
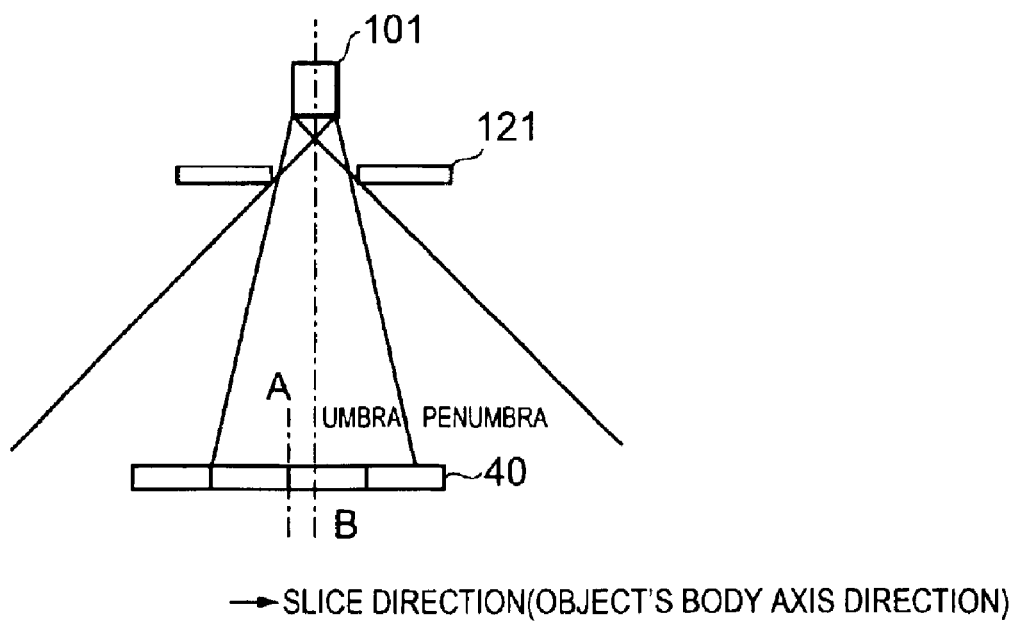
FIG. 5 is an example showing a physical relationship between the X-ray tube and the detector for explaining a penumbra according to the first embodiment of the present invention.

On the other hand, as shown in FIG. 5, when the central axis B is construed as a symmetry axis, a penumbra is deemed to be an X-ray radiation field, outside of and excluding the umbra, between a line extended from one end of the X-ray tube 101 through an end of the aperture of the slit 121 on the other side to the central axis B and a line extended from the other end of the X-ray tube 101 through the other end of the aperture of the slit 121.

In the umbra, X-ray intensity may be even while X-ray intensity in the penumbra may be different, depending on location. When the central axis B of the X-ray beam irradiated from the X-ray tube 101 and the center A of the detecting segments 40 of the detector 103 are out of alignment in the slice direction, as shown in FIG. 5, detecting segments to be used under such condition cannot be placed symmetrically within the umbra field. This condition disturbs acquisition of preferable tomographs.

Figure 6:
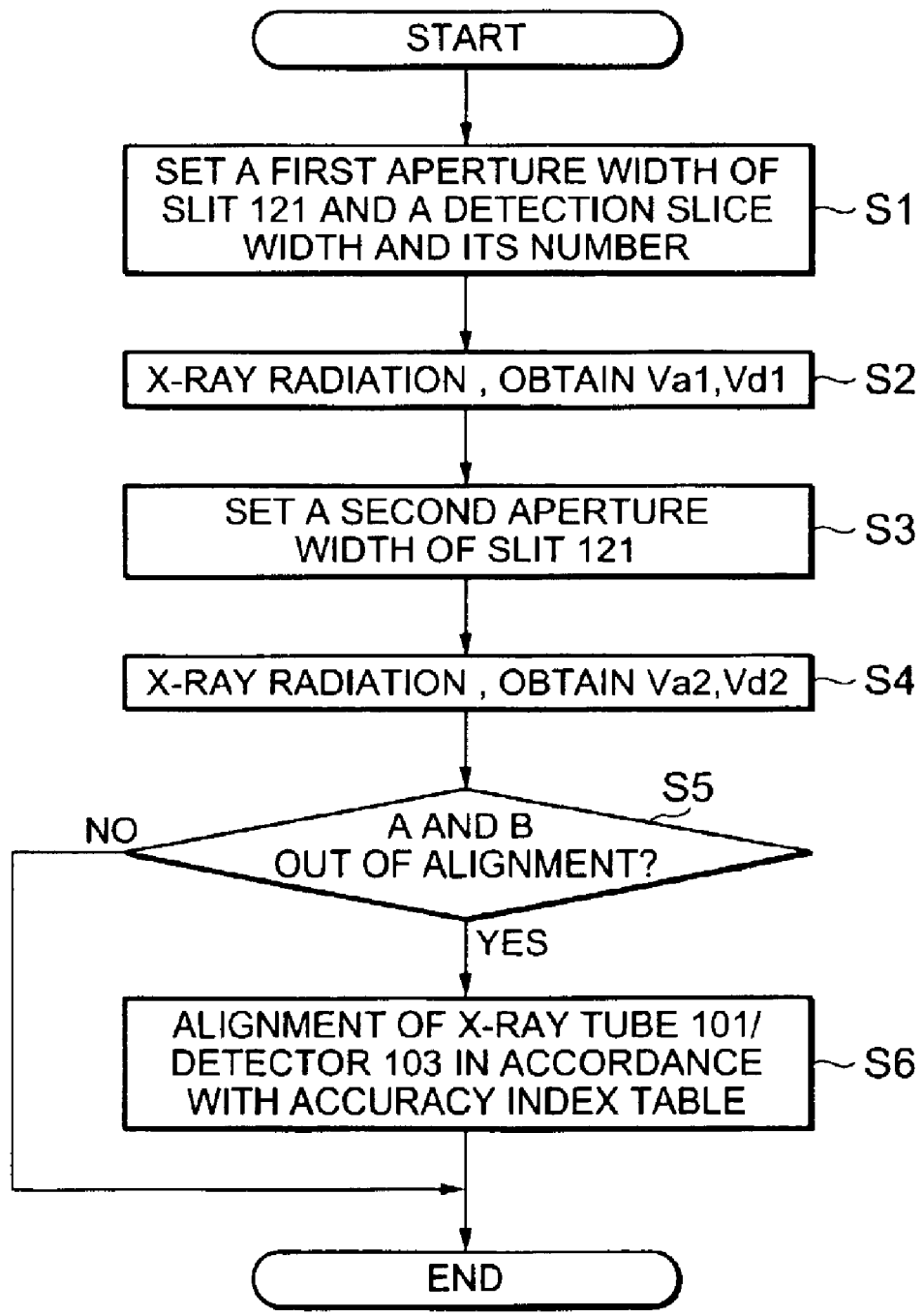
FIG. 6 is a flowchart showing alignment processing procedures in the CT apparatus according to the first embodiment of the present invention.

FIG. 6 is a flowchart showing alignment processing procedures in the CT apparatus 10 according to the first embodiment of the present invention. The X-ray tube 101 and the slit 121 are fixed in a conventional manner. The aperture of the slit 121 may be set to a width, as a first aperture width, which allows the detector 103 to obtain 0.5 mm×4 slices (the width of each slice: 0.5 mm) while the detector 103 may be prepared to obtain 2 mm×4 slices (the width of each slice: 2 mm). That is, the first aperture width set at the slit 121 is narrower than an aperture width required exposing to the width actually prepared at the detector 103 (step S1).

Figure 7:
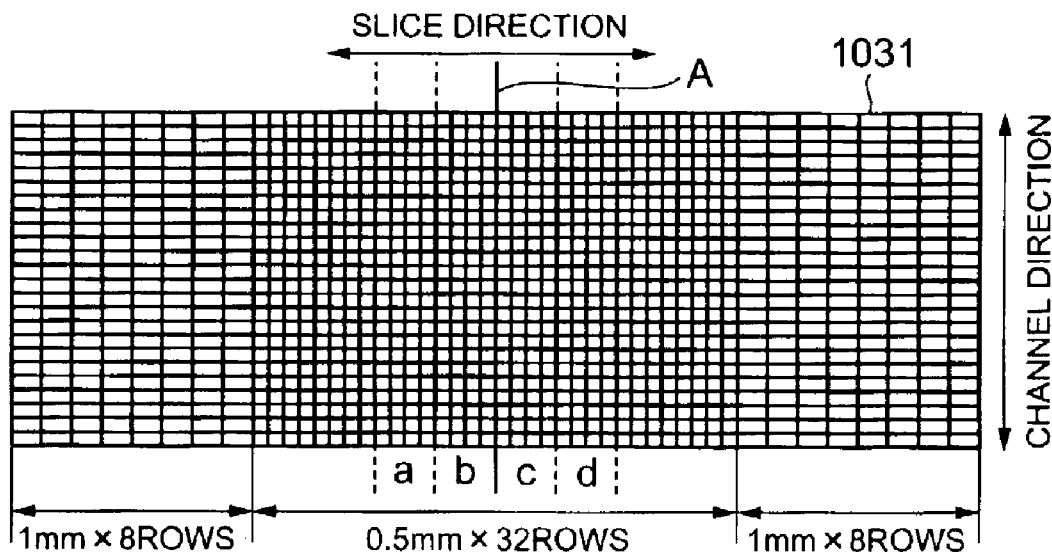
FIG. 7 is an example showing detecting elements of the detector according to the first embodiment of the present invention.

FIG. 7 is an example showing detecting elements in a detection block of the detector 103. A detection block 1031 comprises a 0.5 mm detecting element area, and two 1 mm detecting element areas, each of which is provided at each side of the 0.5 mm detecting element area along the slice direction. The 0.5 mm detecting element area comprises 32 detecting element rows, each of which is wide enough to detect a 0.5 mm width slice. This indicates that each detecting element has a width to be able to detect a 0.5 mm width slice. Further, the 0.5 mm detecting element area comprises tens of detecting elements along the channel direction. Each of the 1 mm detecting element areas comprises 8 detecting element rows, each of which is wide enough to detect a 1 mm width slice. This indicates that each detecting element has a width to be able to detect a 1 mm width slice. Further, each of the 1 mm detecting element areas comprises tens of detecting elements along the channel direction. Here, since the width of each slice has been determined as 2 mm in step S1, four detecting element rows are assigned to each slice as a detecting segment. Also in step S1, the number of slices has been determined as four. Therefore, sixteen detecting element rows are assigned to detecting segments a to d as a whole. It may be a preferable assignment that the detecting segments a and b and the detecting segments c and d are placed symmetrically to each other in reference to the center A of the 0.5 mm detecting element area along the slice direction.

Figure 8:
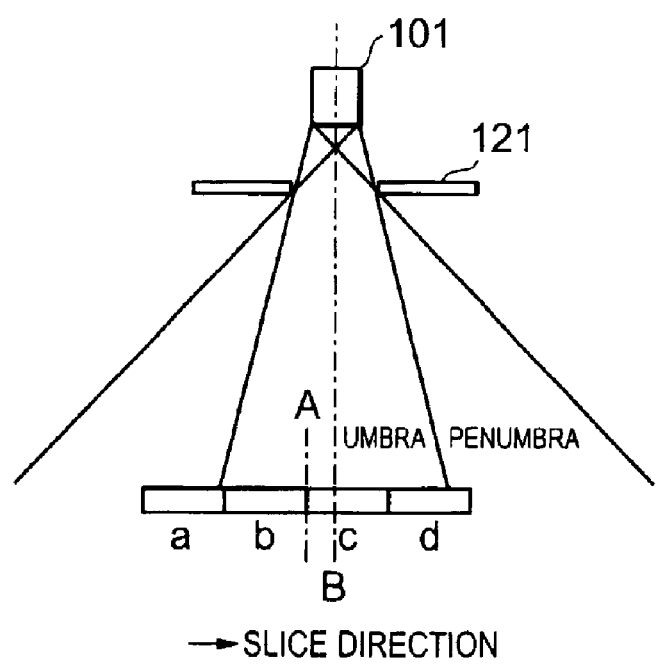
FIG. 8 is an example showing a physical relationship between the X-ray tube and the detector, with a first aperture width of a slit, according to the first embodiment of the present invention.

Next, an X-ray is irradiated from the X-ray tube 101. The irradiated X-ray is collimated by the slit 121 and the collimated X-ray is exposed to the detector 103. Each of the detecting segments a to d detects an X-ray exposed to the each detecting segment. A value Va1 detected in the detecting segment a and a value Vd1 detected in the detecting segment d may be obtained (step S2). In this radiation, the aperture width of the slit 121 is not set to be wide enough to expose to a whole detecting field comprising the detecting segments a to d. Therefore, as shown in FIG. 8, the detecting segments b and c are exposed the X-ray and are covered by the umbra of the X-ray, and the detecting segments a and d are exposed the X-ray and are covered by the umbra in part and also the penumbra in other part, of the X-ray.

In the X-ray detection for the alignment processing in steps S2 and S4, according to the first embodiment of the present invention, the X-ray detection may be implemented without rotating the X-ray tube 101 and the detector 103. Such detection may make possible to achieve a preferable alignment. If, however, more segments are used for the X-ray detection, the X-ray tube 101 and the detector 103 can be rotated in steps S2 and S4.

In step S3, the aperture width of the slit 121 is changed to be wide enough to expose the detecting segments a to d (enough to cover a whole part of the detecting segments a to d). This time, the aperture of the slit 121 may be set to be a width, as a second aperture width, equivalent of obtaining 8 mm×4 slices data.

Figure 9:
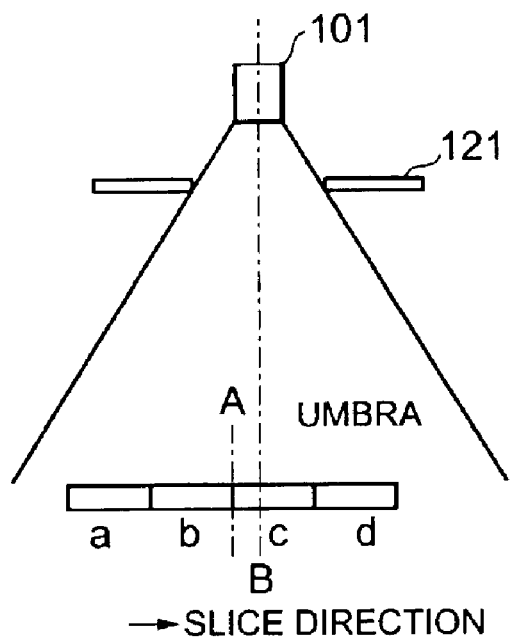
FIG. 9 is an example showing a physical relationship between the X-ray tube and the detector, with a second aperture width of the slit, according to the first embodiment of the present invention.

With the second aperture width of the slit 121, an X-ray is irradiated from the X-ray tube 101. The irradiated X-ray is collimated by the slit 121 and the collimated X-ray is exposed to the detector 103. Each of the detecting segments a to d detects an X-ray exposed to the each segment. A value Va2 detected in the detecting segment a and a value Vd2 detected in the detecting segment d may be obtained (step S4). In this radiation, the second aperture width of the slit 121 is set to be wide enough to expose to a whole detecting field comprising the detecting segments a to d. Therefore, as shown in FIG. 9, the detecting segments a to d are exposed the X-ray and are covered by the umbra of the X-ray.

After the detection in step S4, the host controller 110 determines whether the central axis B of the X-ray irradiated from the X-ray tube 101 and the center A of the detecting segments a to d of the detector 103 are out of alignment in the slice direction or not (step S5). Upon this determination, an index is calculated on the basis of the detected values Va1, Va2, Vd1, and Vd2. The index may indicate the symmetric property, to the center A of the using detecting segments a to d, of between the position of the detecting segment a and the position of the detecting segment d. The index may be used for the above alignment determination. This index may not be limited to a predetermined one as long as it can be used for such a determination. The following is an example of the index. Using the detected values Va1 and Vd1, a first detection ratio R1 according to the detection in step S2 may be obtained as R1=Va1/Vd1. Similarly, a second detection ratio R2 according to the detection in step S4 may be obtained as R2=Va2/Vd2. The difference D between the first detection ratio R1 and the second detection ratio R2 is expressed as D=R1−R2. The more the central axis B of the X-ray irradiated from the X-ray tube 101 and the center A of the detecting segments a to d of the detector 103 are out of alignment in the slice direction, the bigger the difference D is. And vice versa. In this sense, the difference D can be the index explained above. In practice, however, it may be impossible to align the X-ray tube 101 and the detector 103 perfectly without any misalignment. Therefore, it may be determined to be acceptable if the index D is within a predetermined range, for example, within the 15 percent. The detected values Va1, Va2, Vd1, and Vd2 and the calculated index D may be stored in the alignment data storing unit 120.

In step S5, when the index D is within the 15 percent, the host controller 110 may determine that it is not necessary to correct the current position arrangement of the X-ray tube 101 and the detector 103. Responsive to this determination, the processing for the alignment may be ended. On the other hand, if the index D is over the 15 percent, the host controller 110 may determine that it is necessary to correct the current position arrangement of the X-ray tube 101 and the detector 103. Responsive to this determination, the processing may be forwarded to step S6 for the alignment. In step S6, the host controller 110 obtains a distance to adjust the position arrangement of the X-ray tube 101 and the detector 103 along the slice direction (or simply a current distance between the central axis B of the X-ray irradiated from the X-ray tube 101 and the center A of the detecting segments a to d of the detector 103 in the slice direction), and also determines in which direction at least one of the X-ray tube 101 and the detector 103 should be moved so as to align them. These may be made based on the index D stored in the alignment data storing unit 120 and the alignment accuracy index table stored in the accuracy index table storing unit 116. The host controller 110 applies the index D to the alignment accuracy index table and determines the above-mentioned distance and the direction.

Figure 10:
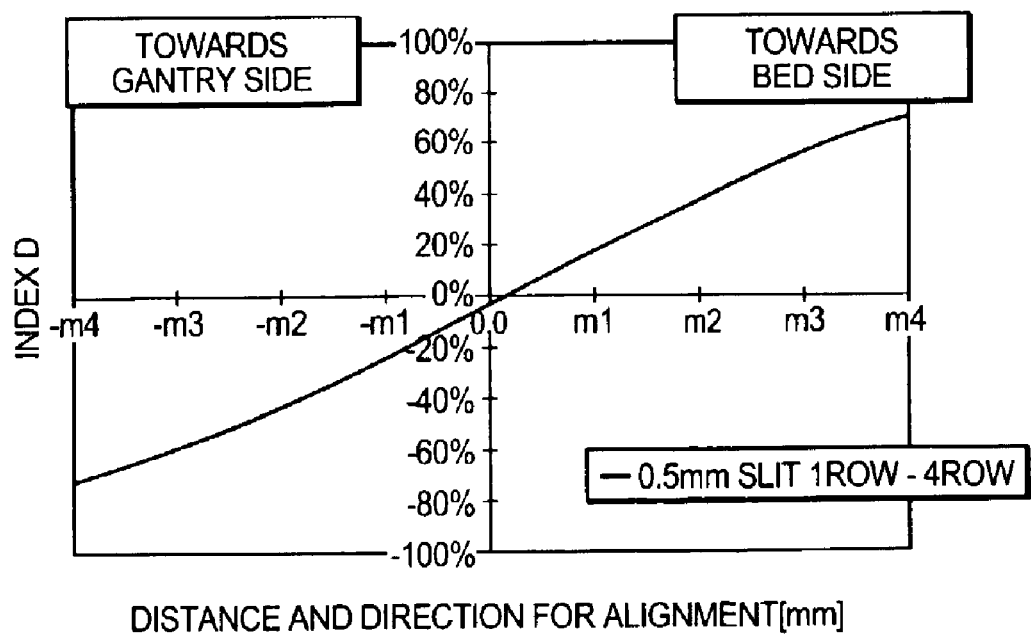
FIG. 10 is a table showing an example of an alignment accuracy index table according to the first embodiment of the present invention.

FIG. 10 is a table showing an example of the alignment accuracy index table stored in the accuracy index table storing unit 116 according to the first embodiment of the present invention. This alignment accuracy index table shows distances and directions to move the detector 103 in order to align the center A of the detecting segments a to d of the detector 103 with the central axis B of the X-ray irradiated from the X-ray tube 101 in the slice direction. The distance and the direction to move are determined by applying the index D to the table. In FIG. 10, when the index D obtained in step S5 shows about 40 percent, the alignment accuracy index table shows that the distance to move may be about m2 [m] and the direction to move should be towards a bed side (e.g., a side of the object's feet) along the slice direction (along the object's body axis direction). In another case, if the index D obtained in step S5 shows about −25 percent, the alignment accuracy index table shows that the distance to move may be about m1 [mm] and the direction to move should be towards a gantry side (e.g., a side of the object's head) (the opposite side of the bed side) along the slice direction (along the object's body axis direction). The host controller 110 may determine the above distance and direction and, if necessary, may control the display unit 119 to display the obtained distance and direction for the alignment.

When the detector 103 is manually moved for the alignment by the operator, the operator refers to the distance and the direction displayed in the display unit 119 and moves the detector 103. If the CT apparatus 10 has a feature to automatically move or adjust the position of the detector 103 along the slice direction, the host controller 110 controls, according to the feature, to move the detector 103 in accordance with the obtained distance and the direction.

In the above example with reference to FIG. 10, it has been described that the accuracy index table storing unit 116 stores the alignment accuracy index table for moving the detector 103 and the detector 103 is moved for the alignment. According to the first embodiment of the present invention, however, the accuracy index table storing unit 116 may (also) store the alignment accuracy index table for moving the X-ray tube 101 and the X-ray tube 101 may be moved for the alignment. Since the X-ray tube 101 is usually fixed and adjustable with adjustable screws and lighter than the detector 103 in weight, it may be easier to move and adjust the X-ray tube 101 than the detector 103.

Further, the index in the alignment accuracy index table may vary, for example, according to kinds of the X-ray tube 101, particularly to the size of a focal point of the X-ray tube 101. Therefore, it may be necessary to store a plurality of alignment accuracy index tables corresponding to kinds of the focal points to be used for the X-ray tube 101, in the accuracy index table storing unit 116.

In the first embodiment of the present invention, the detecting segments a and d have been used for obtaining the index D, and have been the symmetrically furthest detecting segments from the center A of the detector 103. This is because it may be more useful to improve the accuracy of the index D. The alignment processing, however, according to the first embodiment of the present invention, can be effective as long as the index D is obtained on the basis of detections by two of the detecting segments, each of which are in a position symmetrical to the center A of the detector 103, each other.

As explained above, according to the first embodiment of the present invention, it may be possible to align the central axis B of the X-ray irradiated from the X-ray tube 101 and the center A of the detecting segments a to d of the detector 103 in the slice direction. Accordingly, it leads to more accurate radiography. Further, it may make possible to effectively expose the X-ray to detecting segments to be used in an actual radiography, with a minimum aperture width of the slit 121, which results in minimizing the X-ray exposure to the object P.

(Second Embodiment)

In a second embodiment of the present invention, with reference to FIG. 2 again, a system is described that remotely monitors a physical alignment relationship between an X-ray tube and a detector of a CT apparatus.

In FIG. 2, the host controller 110 regularly determines whether the central axis B of the X-ray irradiated from the X-ray tube 101 and the center A of the detecting segments a to d of the detector 103 are out of alignment in the slice direction or not. This is equivalent of the determination in step S5 in FIG. 6. The determination result including the index D may be stored in the alignment data storing unit 120 in each determination, and also be transmitted through the network communication unit 122 to remote monitoring equipment provided at a remote place. The equipment may be placed at and used by a service provider who provides a CT maintenance service to the CT apparatus 10.

The service provider may be able to regularly know the current condition of the CT apparatus regarding the alignment of between the central axis B of the X-ray irradiated from the X-ray tube 101 and the center A of the detecting segments a to d of the detector 103, based on the determination results transmitted from the CT apparatus 10. Accordingly, the service provider may be able to promptly provide an appropriate maintenance service to the CT apparatus 10. Practically, for example, by monitoring the transmitted determination results at predetermined intervals, the service provider may send out service personnel to the CT apparatus 10 in response to an indication of misalignment in the monitored determination results.

(Third Embodiment)

The first and second embodiments of the present invention have been described about the determination with the index D. The determination, however, may also be made with, for example, a use of index obtained by calculating a physical value regarding the center A of the detector 103 on the basis of the values detected in the detecting segments a to d.

Figure 11:
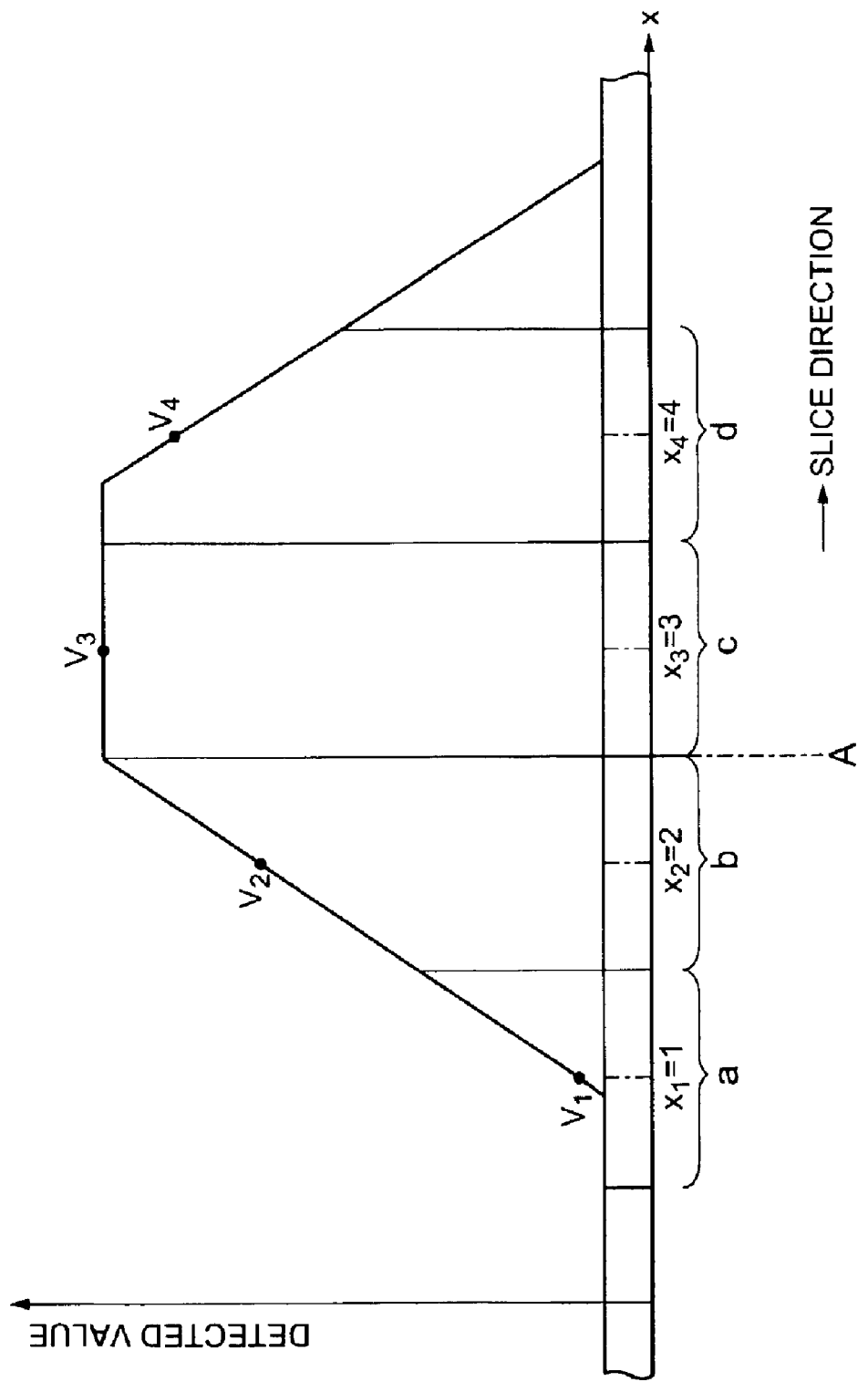
FIG. 11 is a chart showing an example of a relation between detected values in detecting segments of the detector and positions of the detecting segments according to a third embodiment of the present invention.

FIG. 11 is a chart showing an example of a relation between detected values in the detecting segments a to d and positions of the detecting segments a to d according to a third embodiment of the present invention. As shown in FIG. 11, when the slice direction is represented with x axis and a predetermined position may be determined as zero (0) of the x axis, each center of the detecting segments a to d may be represented with x1, x2, x3, and x4 in the x axis. If detected values in the detecting segments a to d are, for example, V1, V2, V3, and V4, respectively, its actual gravity point G may be expressed as follows:

$$G=(x1V1+x2V2+x3V3+x4V4)/(V1+V2+V3+V4).$$

When x1, x2, x3, and x4 are 1, 2, 3, and 4, respectively, the center A of the detector 103 can obviously be 2.5. Therefore, the theoretical gravity point is 2.5. Further, the above expression is expressed as G=(V1+2V2+3V3+4V4)/(V1+V2+V3+V4). When the detected values V1, V2, V3, and V4 are obtained as a result of an X-ray exposure to the detecting segments a to d, the actual gravity point G is obtained according to the above expression. The difference between the theoretical gravity point (2.5) and the actual gravity point G can be a distance due to misalignment of between the central axis B of the X-ray irradiated from the X-ray tube 101 and the center A of the detecting segments a to d of the detector 103 in the slice direction.

In the third embodiment of the present invention, the way of obtaining the actual gravity point G is not limited to that described above. Each center of the detecting segments a to d may be, for example, measured from the center A of the detector 103, by determining the center A as a reference position. Further, the detected values may be values obtained either by the X-ray radiation shown in FIGS. 8 and 9, wherein the detected values may be, for example, a ratio between a detected value in the X-ray radiation shown in FIG. 8 and a detected value in the X-ray radiation shown in FIG. 9, or by the X-ray radiation shown only in FIG. 8, according to the third embodiment of the present invention.

The slit 121 may not be required to be independent from the X-ray tube but included in other component according to the embodiments of the present invention.

Figure 12:
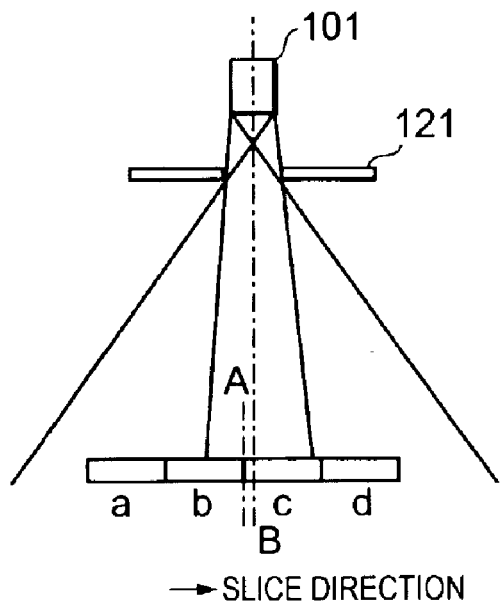
FIG. 12 is another example showing a physical relationship between the X-ray tube and the detector, with another aperture width of a slit, according to the first embodiment of the present invention.

In the first embodiment of the present invention, a example of the X-ray exposure to the detecting segments of the detector 103 with the first aperture width of the slit 121 has been explained with reference to FIG. 8. Embodiment of the present invention may not be limited to such an example. For example, FIG. 12 is another example showing a physical relationship between the X-ray tube 101 and the detector 103, with another aperture width of the slit 121, according to the first embodiment of the present invention. As shown in FIG. 12, the detecting segments b and c may be exposed to the X-ray and covered by the umbra in part and also the penumbra in other part, of the X-ray, while the detecting segments a and d may be only covered by the penumbra of the X-ray. In this example, it may also be possible to obtain a valid index as the index D by calculation with detections by the detecting segments a and d.

Figure 13:
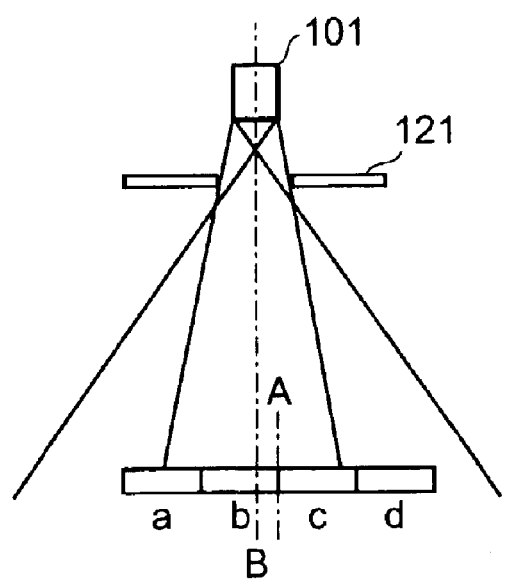
FIG. 13 is still another example showing a physical relationship between the X-ray tube and the detector, with another aperture width of a slit, according to the first embodiment of the present invention.

Still further, for example, FIG. 13 is still another example showing a physical relationship between the X-ray tube 101 and the detector 103, with another aperture width of the slit 121, according to the first embodiment of the present invention. As shown in FIG. 13, the detecting segments a and c may be exposed the X-ray and be covered by the umbra in part and also the penumbra in other part, of the X-ray, and the detecting segment b may be exposed the X-ray and be covered by only the umbra of the X-ray. In addition, the detecting segment d may be exposed the X-ray and be covered by only the penumbra of the X-ray. In this example, it may also be possible to obtain a valid index as the index D by calculation with detections by the detecting segments a and d.

The embodiments of the present invention described above are examples described only for making it easier to understand the present invention, and are not described for the limitation of the present invention. Consequently, each component and element disclosed in the embodiments of the present invention may be redesigned or modified to its equivalent within a scope of the present invention. Furthermore, any possible combination of such components and elements may be included in a scope of the present invention as long as an advantage similar to those obtained according to the above disclosure in the embodiments of the present invention is obtained.

What is claimed is:

1. An X-ray computed tomography apparatus for providing information of alignment, comprising:

an X-ray generator configured to generate an X-ray;

an X-ray detector, comprising a plurality of detecting segments along a slice direction, and configured to detect the X-ray generated by the X-ray generator; and a controller configured to calculate a gravity point of the plurality of detecting segments based on detection information obtained from the plurality of detecting segments and position information of the plurality of detecting segments relative to a predetermined reference position, to obtain a difference between the calculated gravity point and a theoretical gravity point of the plurality of detecting segments, and to provide the difference as the information of alignment between the X-ray generator and the X-ray detector along the slice direction.

2. The apparatus according to claim 1, further comprising a display configured to display the information of alignment provided by the controller.

3. The apparatus according to claim 1, further comprising a communication interface configured to transmit the information of alignment provided by the controller to an external monitoring apparatus.

4. The apparatus according to claim 1, wherein the alignment between the X-ray generator and the X-ray detector is performed between a central axis of the X-ray generated from the X-ray generator and a center of the detecting segments of the X-ray detector along the slice direction.

5. An X-ray computed tomography apparatus for providing information of alignment, comprising:

an X-ray generator configured to generate an X-ray;

an X-ray detector, including a plurality of detecting segments along a slice direction, configured to detect the X-ray generated by the X-ray generator;

a controller coupled to the detector and configured to obtain a calculation index based on calculation of a first ratio from penumbra detection information obtained from first and second of the detecting segments when the first and second detecting segments are exposed to the X-ray and at least partially covered by first and second penumbras of the X-ray, respectively, and a second ratio from umbra detection information obtained from the first and second detecting segments when both of the first and second detecting segments are exposed to the X-ray and covered by only an umbra of the X-ray, the first detecting segment opposing the second detecting segment relative to a center of the detecting segments; and a memory coupled to the controller and configured to store a table including a relation between a table index and shift information for shifting at least one of the X-ray generator and the X-ray detector so as to align the X-ray generator and the X-ray detector, wherein the controller determines the shift information corresponding to the table index based on the calculation index, and wherein, when each of the first and second detecting segments comprises a plurality of detecting elements, the penumbra detection information is a bundle of element detection information obtained from the plurality of detecting elements.

6. An X-ray computed tomography apparatus for providing information of alignment, comprising:

an X-ray generator configured to generate an X-ray;

an X-ray detector, including a plurality of detecting segments alone a slice direction, configured to detect the X-ray generated by the X-ray generator;

a controller coupled to the detector and configured to obtain a calculation index based on calculation of a first ratio from penumbra detection information obtained from first and second of the detecting segments when the first and second detecting segments are exposed to the X-ray and at least partially covered by first and second penumbras of the X-ray, respectively, and a second ratio from umbra detection information obtained from the first and second detecting segments when both of the first and second detecting segments are exposed to the X-ray and covered by only an umbra of the X-ray, the first detecting segment opposing the second detecting segment relative to a center of the detecting segments; and a memory coupled to the controller and configured to store a table including a relation between a table index and shift information for shifting at least one of the X-ray generator and the X-ray detector so as to align the X-ray generator and the X-ray detector, wherein the controller determines the shift information corresponding to the table index based on the calculation index, and wherein the first and second detecting segments are physically situated around the center of the detecting segments.

7. An X-ray computed tomography apparatus for providing information of alignment, comprising:

an X-ray generator configured to generate an X-ray;

an X-ray detector, including a plurality of detecting segments alone a slice direction, configured to detect the X-ray generated by the X-ray generator;

a controller coupled to the detector and configured to obtain a calculation index based on calculation of a first ratio from penumbra detection information obtained from first and second of the detecting segments when the first and second detecting segments are exposed to the X-ray and at least partially covered by first and second penumbras of the X-ray, respectively, and a second ratio from umbra detection information obtained from the first and second detecting segments when both of the first and second detecting segments are exposed to the X-ray and covered by only an umbra of the X-ray, the first detecting segment opposing the second detecting segment relative to a center of the detecting segments; and a memory coupled to the controller and configured to store a table including a relation between a table index and shift information for shifting at least one of the X-ray generator and the X-ray detector so as to align the X-ray generator and the X-ray detector, wherein the controller determines the shift information corresponding to the table index based on the calculation index, and wherein the first detecting segment is provided at one end of the detecting segments and the second detecting segment is provided at another end of the detecting segments.

8. A method of providing information of alignment between an X-ray generator and an X-ray detector of an X-ray computed tomography apparatus, wherein the X-ray generator generates an X-ray and the X-ray detector includes a plurality of detecting segments along a slice direction and detects the X-ray generated by the X-ray generator, the method comprising the steps of:

obtaining detection information from the plurality of detecting segments;

calculating a gravity point of the plurality of detecting segments based on the detection information and position information of the plurality of detecting segments relative to a predetermined reference position;

obtaining a difference between the calculated gravity point and a theoretical gravity point of the plurality of detecting segments; and providing the difference as the information of alignment along the slice direction.

9. An X-ray computed tomography apparatus for providing information of alignment, comprising:

an X-ray generator configured to generate an X-ray;

an X-ray detector, including a plurality of detecting segments along a slice direction, configured to detect the X-ray generated by the X-ray generator;

a controller coupled to the detector and configured to obtain a calculation index based on calculation of a first ratio from penumbra detection information obtained from first and second of the detecting segments when the first and second detecting segments are exposed to the X-ray and at least partially covered by first and second penumbras of the X-ray, respectively, and a second ratio from umbra detection information obtained from the first and second detecting segments when both of the first and second detecting segments are exposed to the X-ray and covered by only an umbra of the X-ray, the first detecting segment opposing the second detecting segment relative to a center of the detecting segments; and a memory coupled to the controller and configured to store a table including a relation between a table index and shift information for shifting at least one of the X-ray generator and the X-ray detector so as to align the X-ray generator and the X-ray detector, wherein the controller determines the shift information corresponding to the table index based on the calculation index, and wherein the first detecting segment is exposed to the X-ray by the X-ray generator and is covered only by the first penumbra and the second detecting segment is exposed to the X-ray by the X-ray generator and is covered only by the second penumbra for the calculation of the first ratio.

10. An X-ray computed tomography apparatus for providing information of alignment, comprising:

an X-ray generator configured to generate an X-ray;

an X-ray detector, including a plurality of detecting segments along a slice direction, configured to detect the X-ray generated by the X-ray generator;

a controller coupled to the detector and configured to obtain a calculation index based on calculation of a first ratio from penumbra detection information obtained from first and second of the detecting segments when the first and second detecting segments are exposed to the X-ray and at least partially covered by first and second penumbras of the X-ray, respectively, and a second ratio from umbra detection information obtained from the first and second detecting segments when both of the first and second detecting segments are exposed to the X-ray and covered by only an umbra of the X-ray, the first detecting segment opposing the second detecting segment relative to a center of the detecting segments; and a memory coupled to the controller and configured to store a table including a relation between a table index and shift information for shifting at least one of the X-ray generator and the X-ray detector so as to align the X-ray generator and the X-ray detector, wherein the controller determines the shift information corresponding to the table index based on the calculation index, and wherein the first detecting segment is exposed to the X-ray by the X-ray generator and is covered only by the first penumbra and the second detecting segment is exposed to the X-ray by the X-ray generator and is covered partially by the second penumbra and partially by an umbra of the X-ray for the calculation of the first ratio.

11. An X-ray computed tomography apparatus for providing information of alignment, comprising:

an X-ray generator configured to generate an X-ray;

an X-ray detector, including a plurality of detecting segments alone a slice direction, configured to detect the X-ray generated by the X-ray generator;

a controller coupled to the detector and configured to obtain a calculation index based on calculation of a first ratio from penumbra detection information obtained from first and second of the detecting segments when the first and second detecting segments are exposed to the X-ray and at least partially covered by first and second penumbras of the X-ray, respectively, and a second ratio from umbra detection information obtained from the first and second detecting segments when both of the first and second detecting segments are exposed to the X-ray and covered by only an umbra of the X-ray, the first detecting segment opposing the second detecting segment relative to a center of the detecting segments; and a memory coupled to the controller and configured to store a table including a relation between a table index and shift information for shifting at least one of the X-ray generator and the X-ray detector so as to align the X-ray generator and the X-ray detector, wherein the controller determines the shift information corresponding to the table index based on the calculation index, and wherein the first detecting segment is exposed to the X-ray by the X-ray generator and is covered partially by the first penumbra and partially by an umbra of the X-ray and the second detecting segment is exposed to the X-ray by the X-ray generator and is covered partially by the second penumbra and partially by the umbra of the X-ray for the calculation of the first ratio.

* * * * *